United States Patent
Rautschek

(10) Patent No.: US 8,475,777 B2
(45) Date of Patent: Jul. 2, 2013

(54) SILICONE EMULSIONS, AND METHODS FOR THE PRODUCTION THEREOF

(75) Inventor: Holger Rautschek, Nuenchritz (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 13/394,388

(22) PCT Filed: Aug. 31, 2010

(86) PCT No.: PCT/EP2010/062667
§ 371 (c)(1),
(2), (4) Date: Mar. 6, 2012

(87) PCT Pub. No.: WO2011/032824
PCT Pub. Date: Mar. 24, 2011

(65) Prior Publication Data
US 2012/0171147 A1 Jul. 5, 2012

(30) Foreign Application Priority Data
Sep. 16, 2009 (DE) .......................... 10 2009 029 520

(51) Int. Cl.
*A61K 8/72* (2006.01)
(52) U.S. Cl.
USPC ...................................................... 424/70.11
(58) Field of Classification Search
None
See application file for complete search history.

(56) References Cited

U.S. PATENT DOCUMENTS

| 3,294,725 A | | 12/1966 | Findlay et al. | |
|---|---|---|---|---|
| 3,634,285 A | | 1/1972 | Brooks, Howard Larry | |
| 4,194,988 A | * | 3/1980 | Schneider et al. | 516/56 |
| 4,476,282 A | | 10/1984 | Koerner et al. | |
| 4,600,436 A | | 7/1986 | Traver et al. | |
| 6,013,682 A | * | 1/2000 | Dalle et al. | 516/55 |
| 6,448,297 B1 | | 9/2002 | Turowski-Wanke et al. | |

FOREIGN PATENT DOCUMENTS

| DE | 1495512 | 4/1970 |
|---|---|---|
| DE | 2014174 | 10/1970 |
| DE | 2730923 | 1/1979 |
| EP | 0093310 B2 | 1/1998 |
| EP | 1072629 A2 | 1/2001 |
| EP | 1368109 A0 | 12/2003 |
| GB | 1246134 | 9/1971 |
| JP | 2001-288269 A | 10/2001 |
| JP | 2002-20490 A | 1/2002 |
| WO | 02/070112 A2 | 9/2002 |
| WO | 2006/010210 A1 | 2/2006 |

* cited by examiner

*Primary Examiner* — Paul Dickinson
(74) *Attorney, Agent, or Firm* — Brooks Kushman P.C.

(57) ABSTRACT

Emulsions of high viscosity silicones are prepared by emulsifying a lower viscosity condensable silicone with a partial phosphate ester surfactant, and ripening the emulsion to obtain a higher viscosity silicone dispersed phase without generation of objectional amounts of octaorganocyclotetrasiloxanes. The emulsions are well suited for body care products.

22 Claims, No Drawings

SILICONE EMULSIONS, AND METHODS FOR THE PRODUCTION THEREOF

CROSS-REFERENCE TO RELATED APPLICATIONS

This application is the U.S. national phase of PCT Appln. No. PCT/EP2010/062667 filed Aug. 31, 2010, claims priority to German Patent Application No. DE 10 2009 029 520.8 filed Sep. 16, 2009.

BACKGROUND OF THE INVENTION

1. Field of the Invention

The invention relates to aqueous silicone emulsions which comprise high-viscosity polyorganosiloxanes and have a particularly low content of cyclic siloxanes, to methods for the production thereof, and to the use thereof.

2. Description of the Related Art

Silicones can be used widely. In order to facilitate the use and dosing, especially in the case of viscous products, it is desirable for many applications that the organosilicon compounds are present in dilute form. Although the use of organic solvents, such as benzene or chlorocarbons, is possible for this purpose, it is disadvantageous from an ecological and occupational medicine point of view. Consequently, they are used mostly in the form of aqueous emulsions or dispersions, usually as oil-in-water emulsions (O/W emulsions), which can be diluted with water. The oil phase here is understood as meaning the water-immiscible organosilicon compounds, optionally dissolved in organic solvents.

For many applications, it is advantageous if the silicone has a high molecular weight and thus a high viscosity. A known way to arrive at emulsions which comprise a high molecular weight silicone is the emulsion polymerization of low-molecular weight, in particular cyclic, organosiloxanes with arylalkylsulfonic acids (DE-B 14 95 512). In this process, as a result of intensive stirring or homogenization using a high-pressure homogenizer, extraordinarily low particle sizes are achieved which can no longer be seen using an optical microscope. A disadvantage of this method is the fact that, on account of the equilibrium character of this reaction, based on siloxane, more than 10% volatile cyclic siloxanes are present, but these are undesired. Consequently, it has been proposed to subsequently distill these off (e.g. U.S. Pat. No. 4,600,436) or to remove them using a membrane method (EP-A 1 368 109). Both methods signify additional technical expenditure and can adversely affect the stability of the emulsion.

Alternatively, instead of cyclic siloxanes, linear oligomers with terminal silanol groups can be used. From these oligomers, in the presence of emulsifiers, condensation catalysts and a very small amount of water, a paste is formed in which the polycondensation takes place. This paste is then diluted to the desired concentration (EP 93 310 B2). In general, the fractions of cyclic volatile siloxanes are lower than in the case of the emulsion polymerization of cyclic siloxanes. A reduction in the fraction of these volatile siloxanes can take place e.g. by firstly producing an emulsion from the salt form of the anionic emulsifier/catalyst, and then activating this by adding acid (EP-A 1 072 629). This ultimately increases the salt fraction in the emulsion, which is disadvantageous for the stability. When using alkoxy-terminated siloxane oligomers, likewise fewer cycles are said to be formed (JP-A2001288269). However, these oligomers are more difficult to produce and thus more cost-intensive.

Special emulsifiers based on taurocholates likewise contribute to the reduction in the amount of cycles which are formed during the emulsion condensation of siloxane oligomers (WO 2006102010). However, here too, as the working examples clearly show, more than 1% octamethylcyclotetrasiloxane is formed.

It has also been proposed to emulsify dimethylpolysiloxanes, in particular polysiloxanes which are terminated with trimethylsiloxy groups, with viscosities of up to 5,000,000 cSt by mixing and heating these with 10-30%, based on siloxane, of a phosphoric acid partial ester until a clear solution is formed which, after neutralization, is diluted with water (DE-A 27 30 923). However, this method has the disadvantage that the polydimethylsiloxane is in most cases depolymerized, meaning that the resulting emulsion comprises a low-viscosity siloxane and a high fraction of volatile cyclic siloxanes, e.g. octamethyl-cyclotetrasiloxane.

In JP2002020490 it is proposed to use a two-component combination of emulsifiers comprising polyoxyethylene alkyl sulfates, polyoxyethylene alkyl phosphates and alkylsulfonates or the corresponding acids, in which case the acid is preferably only liberated in the emulsion by adding mineral acids such as sulfuric acid. The sole use of polyoxyethylene alkyl phosphates is said to lead only to low molecular weight polyorgano-siloxanes since their catalytic activity is too low. Consequently, combinations with sulfates or sulfonates and an activation by sulfuric acid are necessary. This leads ultimately in turn to more than 1% cyclic siloxane oligomers unless the reaction time is extremely short, although in this case no viscosities >1,000,000 mm$^2$/s are achieved.

On the other hand, emulsions of this type are in practice often produced by either producing a plurality of batches discontinuously and transferring them to a ripening tank or producing a continuous campaign over a certain period in a ripening tank where then, after reaching the desired viscosity, the reaction is terminated by neutralization. In this connection, it is inevitable that a not inconsiderable part of the emulsion remains in the tank for longer than necessary, as a result of which the fraction of cyclic oligomers exceeds the tolerable level.

SUMMARY OF THE INVENTION

The invention provides emulsions of polyorganosiloxanes comprising
(A) polyorganosiloxanes which have a viscosity greater than 10,000 mm$^2$/s, measured at 25° C.,
(B) at least one emulsifier of the formula $$(RO)_nP(O)(OH)_{(3-n)} \qquad (I)$$

in which
R are identical or different and are monovalent hydrocarbon radicals having 4 to 30 carbon atoms,
n is 1 or 2,
and/or salts thereof
and
(C) water,
with the proviso that the emulsion comprises less than 2% by weight of octaorganylcyclotetrasiloxane (D$_4$), based on component (A).

The invention further provides a method for producing the emulsions according to the invention, wherein
(a) polyorganosiloxanes comprising units of the general formula $$R^2_a(R^1O)_bSiO_{(4-a-b)/2} \qquad (II)$$

in which
R$^2$ are identical or different and are monovalent, optionally substituted hydrocarbon radicals having 1 to 30 carbon atoms, or a hydrogen atom, $R^1$ are identical or different and are hydrogen or a monovalent, optionally substituted hydrocarbon radical,
a is 0, 1, 2 or 3 and
b is 0, 1, 2 or 3,
with the proviso that the sum a+b is less than or equal to 3 and the organopolysiloxanes contain 5 to 500 units of the formula (II),
(b) an emulsifier of the formula (I), the OH groups of which can optionally be partially neutralized,
(c) water and
optionally
(d) further substances
are mixed by stirring and/or homogenization, and the organopolysiloxanes (a) comprising units of the formula (II) are left to condense at temperatures of from 0 to 50° C. until the desired viscosity is reached, and optionally then the emulsifier of the formula (I) is neutralized with bases such that the pH of the emulsion is greater than 5, and optionally further water (c) and/or further substances (d) are added.

DETAILED DESCRIPTION OF THE PREFERRED EMBODIMENTS

The emulsions according to the invention can be produced by methods known to the person skilled in the art.

Mixing and homogenization tools which can be used are all emulsifying devices known to those skilled in the art, for example, high-speed stirrers, dissolver plates, rotor-stator homogenizers, ultrasound homogenizers and high-pressure homogenizers of a wide variety of designs.

The method according to the invention can be operated continuously, semicontinuously or discontinuously.

A preferred embodiment of the method of the invention is one wherein
in a 1st step
(a) 100 parts by weight of polyorganosiloxanes comprising units of the general formula

$$R^2{}_a(R^1O)_b SiO_{(4-a-b)/2} \qquad (II)$$

in which
$R^2$ are identical or different and are monovalent, optionally substituted hydrocarbon radicals having 1 to 30 carbon atoms or hydrogen,
$R^1$ are identical or different and are hydrogen or a monovalent, optionally substituted hydrocarbon radical,
a is 0, 1, 2 or 3 and
b is 0, 1, 2 or 3,
with the proviso that the sum a+b is less than or equal to 3 and the organopolysiloxanes contain 5 to 500 units of the formula (II),
(b) 1 to 30 parts by weight of an emulsifier of the formula (I), the OH groups of which can optionally be partially neutralized,
(c) 1 to 50 parts by weight of water and
optionally
(d) further substances
are mixed by stirring and/or homogenization,
in an optionally carried out 2nd step
further water (c) is added,
in a 3rd step
the organopolysiloxanes (a) comprising units of the formula (II) are left to condense at temperatures of from 0 to 50° C. until the desired viscosity is reached,
in an optionally carried out 4th step
the emulsifier of the formula (I) is neutralized with bases such that the pH of the emulsion is greater than 5 and
in an optionally carried out 5th step
the emulsion obtained in the 4th step is mixed with further water (c) and/or further substances (d).

The polyorganosiloxanes (A) which are present in the emulsions according to the invention are preferably those comprising units of the formula (II), more preferably those of units of the formula (II) with an average value of a of from 1.990 to 2.005 and an average value of b of from 0.001 to 0.004, in particular units of the formula (II) where $R^1$ is a hydrogen atom, $R^2$ is a methyl radical and with an average value of a of from 1.990 to 2.005 and an average value of b of from 0.001 to 0.004. The polyorganosiloxanes (A) are most preferably dimethylpolysiloxanes which carry trimethylsiloxy and/or dimethylhydroxysiloxy end groups.

Polyorganosiloxanes (A) which are present in the emulsions according to the invention have preferably have a viscosity of greater than 100,000 mm$^2$/s, more preferably greater than 1,000,000 mm$^2$/s, in each case at 25° C.

Examples of radicals R are branched or unbranched alkyl radicals having 4 to 30 carbon atoms, such as butyl, hexyl, 2-ethylhexyl, octyl, isononyl, n-decyl, dodecyl, isotridecyl and n-tetradecyl radicals, unsaturated aliphatic radicals, such as oleyl radicals, and also aromatic radicals, such as phenyl, toloyl, xylyl, nonylphenyl, naphthyl, anthracyl, tristyrylphenyl or benzyl radicals.

Preferably, radicals R are alkyl radicals having 4 to 18 carbon atoms, more preferably n-butyl, n-octyl, 2-ethylhexyl, n-decyl, n-dodecyl or n-tetradecyl radicals, in particular, the n-octyl and n-decyl radicals.

Examples of compounds of the formula (I) are di-n-butyl phosphate, di-n-hexyl phosphate, mono-n-octyl phosphate, di-n-octyl phosphate, mono-2-ethylhexyl phosphate, di-2-ethylhexyl phosphate, monoisononyl phosphate, diisononyl phosphate, mono-n-decyl phosphate, n-octyl-n-decyl phosphate, di-n-decyl phosphate, monoisotridecyl phosphate, di-n-nonylphenyl phosphate, monooleyl phosphate and distearyl phosphate. Preferably, the compounds of the formula (I) used are mono-n-octyl phosphate, di-n-octyl phosphate, mono-n-decyl phosphate, n-octyl-n-decyl phosphate and di-n-decyl phosphate. The compounds of formula (I) are preferably mixtures of diesters and monoesters.

The emulsions of the invention can comprise, as component (B), compounds of the formula (I) as such, or salts thereof, preferably with alkali metal or alkaline earth metal hydroxides, ammonia or amines, or mixtures of acids of the formula (I) and salts thereof. Component (B) of the emulsions is preferably a salt of a compound of the general formula (I), in particular an alkali metal salt or triethanolamine salt.

The acid number of the component (B) present in the emulsion is determined by its number of free OH groups and its molar mass, thus determining the amount of KOH in mg which is required to neutralize 1 g of component (B). The acid number of component (B) is preferably in the range from 0 to 200, more preferably in the range from 0 to 20, and in particular 0, i.e. the component(s) (B) comprise completely neutralized compounds of the formula (I).

Compounds of the formula (I) are commercially available and/or can be synthesized by generally known chemical methods.

The emulsions according to the invention advantageously comprise no or a very small fraction of cyclic siloxanes, in particular of octaorganylcyclotetra-siloxanes (D$_4$). The organyl groups in the cyclosiloxanes depend on the organyl groups in the organopolysiloxane used and are preferably methyl groups.

The emulsions preferably comprise less than 1% by weight, more preferably less than 0.5% by weight, of octaorganylcyclotetrasiloxane, in particular octamethylcyclotetrasiloxane ($D_4$), in each case based on component (A).

The emulsions of the invention preferably have a particle diameter of 50 to 1000 nm, more preferably from 100 to 500 nm, and in particular from 100 to 200 nm, this data referring to the average value of the volume distribution measured in accordance with the Fraunhofer diffraction principle (corresponding to ISO 13320).

The emulsions preferably have a content of nonvolatile fractions measured in accordance with DIN EN ISO 3251 of 1 to 80% by weight, more preferably from 10 to 65% by weight, and in particular from 30 to 60% by weight.

The pH of the emulsions is preferably 5 to 10, more preferably 6 to 8, and in particular about 7.

Examples of hydrocarbon radicals $R^2$ are alkyl radical such as the methyl, ethyl, n-propyl, isopropyl, 1-n-butyl, 2-n-butyl, isobutyl, tert-butyl, n-pentyl, isopentyl, neopentyl, and tert-pentyl radicals; hexylradical such as the n-hexyl radical; heptyl radical such as the n-heptyl radical; octyl radical such as the n-octyl radical and isooctyl radical such as the 2,2,4-trimethylpentyl radical; nonyl radical such as the n-nonyl radical; decyl radicals, such as the n-decyl radical; dodecyl radical such as the n-dodecyl radical; octadecyl radical such as the n-octadecyl radical; cycloalkyl radical such as the cyclopentyl, cyclohexyl, cycloheptyl and methylcyclohexyl radicals; alkenyl radical such as the vinyl, 1-propenyl and 2-propenyl radicals; aryl radical such as the phenyl, naphthyl, anthryl and phenanthryl radicals; alkaryl radical such as the o-, m-, p-tolyl radical, xylyl radicals and ethylphenyl radicals; and aralkyl radical such as the benzyl radical, and the α- and β-phenylethyl radicals.

Examples of substituted radicals $R^2$ are radicals substituted with halogen, cyano, glycidoxy, polyalkylene glycol or amino groups, for example, the trifluoropropyl, cyanoethyl, glycidoxy-propyl, polyalkyleneglycolpropyl, aminopropyl or aminoethylaminopropyl radicals.

Preferably, in the units of the formula (II), at most one radical $R^2$ is hydrogen.

Preferably, radicals $R^2$ are hydrocarbon radicals having 1 to 18 carbon atoms, more preferably the methyl or the phenyl radical, where in particular more than 80 mol % of the radicals $R^2$ in the siloxane (a) are methyl radicals.

Examples of radicals $R^1$ are the examples given for radicals $R^2$. Preferably, radical $R^1$ is hydrogen or a hydrocarbon radical having 1 to 4 carbon atoms, more preferably hydrogen atom.

In formula (II), the sum a+b preferably has a value of on average 1.5 to 2.4, particularly preferably on average 1.8 to 2.3, in particular on average 1.9 to 2.1.

The polyorganosiloxanes (a) used in the first step of the inventive method preferably 5 to 500, more preferably contain 10 to 200, and in particular 20 to 100 units of the formula (II).

In preferably 0.4 to 40%, more preferably 2 to 10%, of the units of the formula (II) of the polyroganosiloxanes (a) used in the first step of the method b is not equal to 0.

Examples of siloxanes (a) are polydiorganosiloxanes terminated with alkoxy or hydroxy groups, in particular polydiethyl- and polydimethylsiloxanes. The polyorganosiloxanes (a) preferably have a viscosity of 5 to 10,000 $mm^2/s$, more preferably 10 to 500 $mm^2/s$, and in particular 30 to 100 $mm^2/s$, in each case at 25° C.

Preferably, the siloxanes (a) are those of the formula $$HO[SiR^2{}_2O]_c\text{—}H \quad (III),$$

where $R^2$ has one of the aforementioned meanings, in particular a methyl radical, and c has a value from 5 to 500, preferably from 10 to 200, and more preferably from 20 to 100.

The polyorganosiloxanes (a) comprising units of the formula (II) are standard commercial products and/or can be produced by known methods.

Examples of component (b) are the aforementioned examples of the compounds of the formula (I), optionally in a mixture with salts thereof.

The acid number of the compound of the formula (I) is determined by the average value of n and its molar mass, thus the amount of KOH in mg which is required to neutralize 1 g of compound of the formula (I). The acid number of the compound of the formula (I) is preferably in the range from 100 to 600, more preferably in the range from 200 to 500, in particular in the range from 250 to 450.

Component (b) is preferably used in amounts of 1 to 25 parts by weight, and in particular 2 to 10 parts by weight, in each case based on 100 parts by weight of polyorganosiloxane (a).

As water (c), it is possible to use all types of waters which have also hitherto been used for producing dispersions, preferably partially or completely demineralized, distilled or (repeatedly) redistilled water, waters for medicinal or pharmaceutical purposes, such as e.g. purified water (Aqua purificata as in Pharm. Eur). The water (c) used preferably has a conductivity of less than 50 µS/cm, more preferably less than 10 µS/cm, in particular less than 1.3 µS/cm, in each case at 25° C. and 1010 hPa.

Water (c) is preferably used in the first step of the method according to the invention in amounts of 1 to 30 parts by weight, and in particular 5 to 20 parts by weight, in each case based on 100 parts by weight of polyorganosiloxane (a).

In addition to components (a), (b) and (c), in the first step of the method all further substances (d) which are customarily added to silicone emulsions can now be used, such as e.g. further siloxanes which are different to component (a), silanes, in particular alkoxysilanes, further emulsifiers which are different to component (b), thickeners and/or protective colloids, and also additives, for example, preservatives, disinfectants, wetting agents, corrosion inhibitors, dyes and fragrances. The addition of these components, however, can also take place after a later process step, e.g. after the 5th step.

Examples of further siloxanes (d) which can be used are those of the formula (II) where b is 0, such as e.g. trimethylsiloxy-terminated polydimethylsiloxanes. Such siloxanes (d) are advantageously used in order to control the viscosity of the polysiloxane obtained after the condensation reaction in the emulsion.

If further siloxanes (d) are used, the amounts are preferably 0.01 to 10 parts by weight, based on 100 parts by weight of component (a). In the method according to the invention, preference is given to using no further siloxanes (d).

Examples of silanes (d) which can be used according to the invention are methyltrimethoxysilane, tetraethoxy-silane, vinyltriethoxysilane or hydrolysis/condensation products thereof. Such silanes (d) are advantageously used in order to obtain branched or crosslinked siloxanes, e.g. those which form elastic films after drying the emulsion. These silanes (d) can also be added after the 3rd step.

Examples of further emulsifiers (d) which can be used according to the invention are all emulsifiers known hitherto, such as anionic or nonionic emulsifiers, for example, alkyl sulfates, ethoxylated alkyl sulfates, polyethylene glycol ethers and esters of natural and/or synthetic alcohols or carboxylic acids having 8 to 24 carbon atoms and of natural glycerides, polyethylene glycol ethers of alkylphenols and alkyl polyglycosides.

In the method according to the invention, preferably no cationic and no amphoteric emulsifiers are used, and preferably no further anionic emulsifiers, in particular no alkyl- or alkylarylbenzenesulfonic acids or salts thereof, are used as component (d).

The further emulsifiers (d) optionally used according to the invention are preferably nonionic emulsifiers, for example, all nonionic emulsifiers which have also hitherto been used in silicone emulsions.

The nonionic emulsifiers (d) are most preferably polyoxyethylene glycol ethers or esters, preferably with an HLB value greater than 10, in particular greater than 13, such as polyoxyethylene stearates with to 40 ethylene glycol units and polyoxyethylene isotridecyl ethers having 4 to 40 ethylene glycol units.

If further emulsifiers (d) are used, the amounts are preferably 1 to 20 parts by weight, based on 100 parts by weight of component (a). In the method according to the invention, preferably further emulsifiers (d) are used.

If, in the method according to the invention, thickeners and/or protective colloids are used as component (d), these are preferably acrylic acid copolymers.

If thickeners and/or protective colloids (d) are used, the amounts are preferably 0.01 to 2 parts by weight, based on 100 parts by weight of component (a). In the method according to the invention, preferably no thickener and/or protective colloid (d) is used.

Examples of additives (d) which can be used according to the invention are e.g. preservatives known to the person skilled in the art, dyes or fragrances, in particular preservatives such as methylisothiazolinone, chloromethylisothiazolinone, benzylisothiazolinone, phenoxyethanol, methylparaben, ethylparaben, propyl-paraben, butylparaben, isobutylparaben, alkali metal benzoates, alkali metal sorbates, iodopropynyl butylcarbamate, benzyl alcohol and 2-bromo-2-nitro-propane-1,3-diol.

If additives (d) are used, the amounts are preferably 0.0005 to 2 parts by weight, based on 100 parts by weight of component (a). In the method according to the invention, preferably additives (d) are used.

In the first step of the method according to the invention, all components can be mixed together by stirring and/or homogenization, e.g. in any desired order, the peripheral speed of the stirrer and/or rotor-stator homogenizer being preferably greater than 5 m/s, particularly preferably greater than 10 m/s, in particular 5 to 50 m/s.

Compound of the formula (I) as component (b) can, if desired, already be partially neutralized with bases, in the first step of the method, for example bases such as alkali metal hydroxides or amines, although this is not preferred.

The mixture in the first step of the method has a pH of less than 6, preferably less than 5, more preferably less than 4, and in particular 1 to 3.

Preferably, the emulsion of components (a), (b), (c) and optionally (d) obtained in the first step is highly viscous and non-flowable. It is particularly preferred if the yield point (according to DIN 53019-1 and cited standards) of the emulsion obtained in the first step is greater than 100 Pa, in particular greater than 1000 Pa.

The first step of the method is preferably carried out at temperatures of 5 to 80° C., in particular 10 to 50° C., and at the pressure of the ambient atmosphere, i.e. between 900 and 1100 hPa, or at an increased pressure of up to 20,000 hPa, in particular up to 10,000 hPa.

Preferably, the duration of the first step is less than hours, more preferably less than 2 hours, and in particular 5 to 60 minutes.

The mixture obtained in the first step of the method according to the invention preferably has a particle size (average value of the volume distribution) of less than 1 µm, more preferably 100 to 500 nm, and in particular 100 to 200 nm.

In the optional second step, the emulsion obtained in the first step, particularly if it is of high viscosity to firm consistency, is diluted with water with stirring and/or homogenization such that a flowable emulsion is formed which preferably comprises more than 50 parts by weight of water per 100 parts of component (a). The stirring and/or homogenization can take place under the same conditions as described for the first step.

The second step is preferably carried out at temperatures of 5 to 50° C., in particular 10 to 30° C., and at the pressure of the ambient atmosphere, i.e. between 900 and 1100 hPa, or at an increased pressure of up to 20,000 hPa, in particular of up to 10,000 hPa. The second step can take place in the same container as the first method step.

Preferably, the duration of the optional second step is less than 4 hours, more preferably less than 2 hours, and in particular 5 to 60 minutes. In the inventive method, the second step is preferably practiced.

In the third step of the method, the organopolysiloxanes (a) are left to condense until the viscosity is reached which is desired for siloxane (A) in the emulsion, i.e. a viscosity of greater than 10,000 mm$^2$/s, preferably greater than 100,000 mm$^2$/s, and more preferably greater than 1,000,000 mm$^2$/s, in each case at 25° C.

Preferably, the duration of the third step is 1 to 200 hours, more preferably 8 to 96 hours, and in particular 12 to 72 hours. The third step can take place in the same container as the first and second steps. However, the emulsion can also be transferred to a special container, where optionally a plurality of batches produced one after the other are mixed for the third step. However, it is also possible to carry out the first and second step continuously and the third step in a ripening tank.

The third step of the method is preferably carried out at temperatures of 2 to 30° C., more preferably 5 to 20° C., and at a pressure of the ambient atmosphere, i.e. between 900 and 1100 hPa.

The alcohol optionally produced as condensation byproducts in the method according to the invention, e.g. if $R^1$ in formula (II) is other than a hydrogen atom, can remain in the emulsion or else be removed, for example by distillation in vacuo or by extraction.

Examples of the bases used in the optional fourth step are alkali metal hydroxides, such as NaOH and KOH, and also amines, such as e.g. monoethanolamine and triethanolamine. The pH can in principle also be adjusted by adding alkali metal salts of weak acids, such as e.g. sodium citrate, sodium silicate, potassium acetate or potassium phosphate.

Preferably, the bases which can be used in the fourth step of the process are alkali metal or alkaline earth metal hydroxides, ammonia and amines, preferably NaOH, KOH, monoethanolamine and triethanolamine.

The pH of the emulsion after neutralization is preferably 5 to 10, more preferably 6 to 8, and in particular about 7. The optional fourth step of the method is preferably carried out at temperatures of 5 to 50° C., more preferably 15 to 30° C., and at a pressure of the ambient atmosphere, i.e. between 900 and 1100 hPa. The fourth step is preferably practiced.

The emulsions obtained can now be mixed as desired with further water (c) and/or further substances (d) in an optional 5th step. Preferably, in addition to components (a), (b), (c) and optionally (d), no further components are used.

The components used in the inventive method can, in each case, be a single type of such a component, or else a mixture of two or more types of a particular component.

The emulsions according to the invention or produced according to the invention have the advantage that they comprise highly viscous polydiorganosiloxanes and have a low content of cycles, are very stable and therefore have a long shelf-life.

The emulsions according to the invention or produced according to the invention have the advantage that they are storage-stable and have excellent application properties, such as very good performance as release agents and lubricants, good wetting ability on various substrates, and good conditioning effect in haircare products, i.e. significant reduction in the wet and dry combing force.

The method of the invention has the advantage that emulsions with high molecular weight siloxanes can be produced in a simple and cost-effective manner, and that even after the prolonged duration of the third step, the fraction of cyclic siloxanes remains low, which is particularly favorable e.g. in the case of a continuous production with a wider residence time range.

The method has the further advantage that the viscosity of the oil can be varied within a wide range and can be adjusted easily without an increased fraction of cyclic siloxanes being formed.

The emulsions according to the invention or produced according to the invention can be used for all purposes for which emulsions with highly viscous siloxanes have also hitherto been used, such as, for example, as release agents, lubricants, hydrophobicizing agents and for textile impregnation, in the processing of rubber and plastics or in metalworking, hydrophobicizing agents for glass and mineral construction materials or as a constituent of bodycare products.

The invention further provides bodycare compositions comprising the inventive emulsions in amounts of from 0.05 to 10% by weight, more preferably 0.5 to 5% by weight. Preferably, the bodycare compositions according to the invention are haircare compositions. These haircare compositions preferably comprise one or more conditioners selected e.g. from natural or synthetic waxes, plant oils, mineral oils, fluorinated oils, silicone oils, in particular aminosilicone oils, organic polymers, which may be nonionic, anionic, cationic or amphoteric, cationic proteins and cationic surfactants.

Further ingredients of these haircare compositions are e.g. water, surfactants, organic acids, fragrances, preservatives, vitamins, sunscreens, and further components of haircare compositions known to the person skilled in the art.

The haircare compositions may be e.g. shampoos, rinses, creams, or sprays. These care compositions improve both the dry and the wet combability, and also the feel to the touch in the wet and dry hair. Application can take place e.g. during washing, after washing, as pre- or after-treatment during bleaching or during coloring with direct or oxidation dyes, and during the permanent shaping of hair (e.g. permanent wave). The invention further provides haircare compositions comprising emulsions according to the invention and at least one conditioner.

In the examples below, all parts and percentages refer, unless stated otherwise, to weight. Unless stated otherwise, the examples below are carried out at a pressure of the ambient atmosphere, i.e. at about 1010 hPa, and at room temperature, thus about 25° C. or a temperature which is established when combining the reactants at room temperature without additional heating or cooling. All viscosity data listed in the examples refers to a temperature of 25° C.

The emulsions produced in the examples below were tested as follows:

The particle size was determined by means of dynamic light scattering using a Beckmann-Coulter LS 230. The stated values always refer to the average value of the volume distribution (D[4,3]).

To determine the oil viscosity, 20 g of emulsion were admixed with 30 g of acetone, whereupon the emulsion separated. The acetone/water phase was separated off and the procedure was repeated once more. The polymer was then washed three times with water and dried with stirring at 110° C. until water droplets could no longer be seen, and then after-treated for a further 8 h at 110° C. in a drying cabinet. The viscosity was determined using a cone-plate viscometer MCR 300 (Paar-Physika) at 25° C. and a shear drop of 1/s.

To determine the content of octamethylcyclotetra-siloxane ($D_4$), a $^{29}Si$-NMR spectrum of the emulsion was recorded (Avance 400, Bruker, 10 mm selective $^{29}Si$ NMR sample head, addition of 15% $D_2O$ to the original emulsion, pulse angle 30° waiting time 30 s, 400 scans).

The integrals of the signals between −19.75 to −20 ppm ($D_4$) and −21.5 to −23.25 (remaining D units) were used to ascertain the $D_4$ fraction in mole % of Si which, on account of the same molar mass of the individual siloxane unit (74 g/mol), is practically the same as the fraction of $D_4$ in % by weight, based on polydimethylsiloxanes.

Example 1

100 parts of an α,ω-hydroxy-terminated polydimethyl-siloxane with a viscosity of 60 mPas are introduced as initial charge in a beaker.

Using a rotor-stator homogenizer (Ultra-Turrax, peripheral speed 16 m/s), 6 parts of an n-butyl phosphate with an acid number of 470 mg KOH/g (available under the name "SERVOXYL VPIZ" from Elementis GmbH, D-Cologne), 10 parts of an ethoxylated isotridecyl alcohol (available under the name "Lutensol TO 109" from BASF SE D-Ludwigshafen) and 10 parts of water are added and homogenized for 5 min. The resulting firm gel-like phase had a yield point of 1300 Pa. This phase was homogenized until a particle size less than 500 nm was reached. The emulsion was then diluted with 100 parts of water over the course of 10 min and stored at 15° C. This emulsion had a pH of 1.3. After 72 h, the emulsion is adjusted to a pH of 7 with triethanolamine.

The emulsion obtained in this way is now investigated with regard to particle size, oil viscosity and the content of octamethylcyclotetrasiloxane $D_4$. The results can be found in table 1.

Example 2

100 parts of an α,ω-hydroxy-terminated polydimethyl-siloxane with a viscosity of 60 mPas are introduced as initial charge in a beaker.

Using a rotor-stator homogenizer (Ultra-Turrax, peripheral speed 16 m/s), 10 parts of an octyl decylphosphate with an acid number of 295 mg KOH/g (obtainable under the name "Crodafos 810 A" from Croda GmbH D-Nettetal), 10 parts of an ethoxylated isotridecyl alcohol (available under the name "Lutensol TO 109" from BASF SE D-Ludwigshafen), 3 parts of triethanolamine and 10 parts of water are added and homogenized for 10 min. The resulting gel-like phase (yield point 890 Pa) with a particle size of less than 200 nm is diluted with 100 parts of water over the course of 10 min and stored at 20° C. This emulsion had a pH of 2.8. After 168 h, the emulsion is adjusted to a pH of 7 with triethanolamine.

The emulsion obtained in this way is then investigated with regard to particle size, oil viscosity and the content of octamethylcyclotetrasiloxane $D_4$. The results can be found in table 1.

Example 3

100 parts of an α,ω-hydroxy-terminated polydimethyl-siloxane with a viscosity of 60 mPas are introduced as initial charge in a beaker.

Using a rotor-stator homogenizer (Ultra-Turrax, peripheral speed 16 m/s), 4 parts of an octyl decylphosphate with an acid number of 295 mg KOH/g (available under the name "Crodafos 810 A" from Croda GmbH D-Nettetal), 10 parts of an ethoxylated isotridecyl alcohol (available under the name "Lutensol TO 109" from BASF SE D-Ludwigshafen), 0.2 part of a thickener consisting of a modified polyacrylic acid derivative (available under the name "Pemulen TR 2" from Gattefosse Deutschland GmbH, Weil am Rhein) and 10 parts of water are added and homogenized for 5 min. The resulting gel-like phase (yield point 1520 Pa) with a particle size of less than 200 nm is diluted with 100 parts of water over the course of 10 min and stored at 15° C. This emulsion had a pH of 1.9. After 168 h, the emulsion is adjusted to a pH of 7 with triethanolamine.

The emulsion obtained in this way is now investigated with regard to particle size, oil viscosity and the content of octamethylcyclotetrasiloxane $D_4$. The results can be found in table 1.

Example 4

100 parts of an α,ω-hydroxy-terminated polydimethyl-siloxane with a viscosity of 60 mPas are introduced as initial charge in a beaker.

Using a rotor-stator homogenizer (Ultra-Turrax, peripheral speed 16 m/s), 6 parts of an octyl-decyl phosphate with an acid number of 295 mg KOH/g (available under the name "Crodafos 810 A" from Croda GmbH D-Nettetal), 10 parts of an ethoxylated isotridecyl alcohol (available under the name "Arlypon IT 16 109" from Cognis GmbH Düsseldorf) and 10 parts of water are added and homogenized for 5 min. The resulting gel-like phase (yield point 1120 Pa) with a particle size of less than 200 nm is diluted with 100 parts of water over the course of 10 min and stored at 20° C. This emulsion had a pH of 1.9. After 72 h, the emulsion is adjusted to a pH of 7 with triethanolamine.

The emulsion obtained in this way is now investigated with regard to particle size, oil viscosity and the content of octamethylcyclotetrasiloxane $D_4$. The results can be found in table 1.

Example 5

The procedure described in example 4 is repeated except that the emulsion was only neutralized after 168 h.

The emulsion obtained in this way is now investigated with regard to particle size, oil viscosity and the content of octamethylcyclotetrasiloxane $D_4$. The results can be found in table 1.

Example 6

The procedure described in example 4 is repeated except that only 99 parts of an α,ω-hydroxy-terminated polydimethylsiloxane with a viscosity of 60 mPas are used and additionally 1 part of a trimethylsiloxy-group-terminated polydimethylsiloxane with a viscosity of 350 mm²/s.

The emulsion obtained in this way is then investigated with regard to particle size, oil viscosity and the content of octamethylcyclotetrasiloxane $D_4$. The results can be found in table 1.

Example 7

100 parts of an α,ω-hydroxy-terminated polydimethyl-siloxane with a viscosity of 60 mPas are introduced as initial charge in a beaker.

Using a rotor-stator homogenizer (Ultra-Turrax, peripheral speed 16 m/s), 3 parts of an n-butyl phosphate with an acid number of 470 mg KOH/g (available under the name "SERVOXYL VPIZ" from Elementis GmbH, D-Cologne), 3 parts of a 2-ethylhexyl butylphosphate with an acid number of 310 mg KOH/g (available under the name "SERVOXYL VPTZ" from Elementis GmbH, D-Cologne), 10 parts of an ethoxylated isotridecyl alcohol (available under the name "Lutensol TO 109" from BASF SE D-Ludwigshafen) and 10 parts of water are added and homogenized for 10 min. The resulting firm gel-like phase had a yield point of 2100 Pa. This phase was homogenized until a particle size less than 500 nm was reached. The emulsion was then diluted with 100 parts of water over the course of 15 min and stored at 15° C. This emulsion had a pH of 1.5. After 168 h, the emulsion is adjusted to a pH of 7 with triethanolamine.

The emulsion obtained in this way is now investigated with regard to particle size, oil viscosity and the content of octamethylcyclotetrasiloxane $D_4$. The results can be found in table 1.

Example 8

100 parts of an α,ω-hydroxy-terminated polydimethyl-siloxane with a viscosity of 60 mPas are introduced as initial charge in a beaker.

Using a rotor-stator homogenizer (Ultra-Turrax, peripheral speed 16 m/s), 18 parts of an octyl decylphosphate with an acid number of 295 mg KOH/g (available under the name "Crodafos 810 A" from Croda GmbH D-Nettetal), 3 parts of triethanolamine and 35 parts of water are added and homogenized for 5 min. The resulting viscous phase (yield point 150 Pa) with a particle size of less than 1000 nm is diluted with 100 parts of water over the course of 5 min and stored at 20° C. This emulsion had a pH of 1.7. After 24 h, the emulsion is adjusted to a pH of 7 with triethanolamine.

The emulsion obtained in this way is now investigated with regard to particle size, oil viscosity and the content of octamethylcyclotetrasiloxane $D_4$. The results can be found in table 1.

Example 9

950 kg of an α,ω-hydroxy-terminated polydimethyl-siloxane with a viscosity of 60 mPas are introduced as initial charge in a mixing stirrer with a volume of 2000 l (Becomix RW 2000). The homogenizer is switched on and set at a peripheral speed of 24 m/s. 50 kg of an n-butyl phosphate with an acid number of 470 mg KOH/g (available under the name "SERVOXYL VPIZ" from Elementis GmbH, D-Cologne), 100 kg of an ethoxylated isotridecyl alcohol (available under the name "Lutensol TO 109" from BASF SE D-Ludwigshafen) and 100 parts of water are added and homogenized for 15 min. A firm gel-like phase was formed which had a yield point of 1050 Pa. This phase was homogenized for a further 45 min until a particle size less than 500 nm was reached. The emulsion was then diluted with 900 parts of water over the course of 10 min and stored at 15° C. This emulsion had a pH of 1.3. After 72 h, the emulsion is adjusted to a pH of 7 with triethanolamine. 1.8 kg of preservative based on isothiazolinones (available under the name "Kathon CG" from Acima Chemical Industries Ltd. CH-9471 Buchs/SG) were then added.

The emulsion obtained in this way is now investigated with regard to particle size, oil viscosity and the content of octamethylcyclotetrasiloxane $D_4$. The results can be found in table 1.

Example 10

In a continuous emulsification plant, 1000 kg/h of an α,ω-hydroxy-terminated polydimethylsiloxane with a viscosity of 60 mPas are introduced in parallel as initial charge in a beaker. 60 kg/h of an n-butyl phosphate with an acid number of 470 mg KOH/g (available under the name "SERVOXYL VPIZ" from Elementis GmbH, D-Cologne), 100 kg/h of an ethoxylated isotridecyl alcohol (available under the name "Lutensol TO 109" from BASF SE D-Ludwigshafen) and 100 kg/h of water are metered into a rotor-stator homogenizer which has a peripheral speed of 30 m/s. After this homogenizer, 1000 kg/h of water are metered in and homogenized in a second mixer. The resulting emulsion is pumped continuously to a 10 m³ storage tank and stored therein with stirring at 15° C. After 60 h, the emulsion is adjusted to a pH of 7 with triethanolamine.

The emulsion obtained in this way is now investigated with regard to particle size, oil viscosity and the content of octamethylcyclotetrasiloxane $D_4$. The results can be found in table 1.

Example 11

100 parts of an α,ω-hydroxy-terminated polydimethyl-siloxane with a viscosity of 60 mPas are introduced as initial charge in a beaker.

Using a paddle stirrer, 18 parts of an octyl decylphosphate with an acid number of 295 mg KOH/g (available under the name "Crodafos 810 A" from Croda GmbH D-Nettetal), 3 parts of triethanolamine and 75 parts of water are added and stirred for 5 min. The resulting coarse emulsion is diluted with 100 parts of water over the course of 5 min and then homogenized using a laboratory high-pressure homogenizer (APV 1000 from APV Deutschland GmbH, D-Unna) at a homogenization pressure of 600 bar. The finely divided emulsion is stored for 48 h at 20° C. and then adjusted to a pH of 7 with triethanolamine.

The emulsion obtained in this way is now investigated with regard to particle size, oil viscosity and the content of octamethylcyclotetrasiloxane $D_4$. The results can be found in table 1.

Comparative Example C1

100 parts of an α,ω-hydroxy-terminated polydimethyl-siloxane with a viscosity of 60 mPas are introduced as initial charge in a beaker.

Using a rotor-stator homogenizer (Ultra-Turrax, peripheral speed 16 m/s), 6 parts of alkylbenzene-sulfonic acid (available under the name "Marlonsaure AS 3" from SASOL AG, D-Marl) and 7 parts of water are added and homogenized for 10 min. The resulting gel-like phase is diluted with 100 parts of water over the course of 5 min and stored at 20° C. After 6 h, the emulsion is adjusted to a pH of 7 with triethanolamine.

The emulsion obtained in this way is now investigated with regard to particle size, oil viscosity and the content of octamethylcyclotetrasiloxane $D_4$. The results can be found in table 1.

Comparative Example C2

The procedure described in example C1 is repeated except that the emulsion was only neutralized after 168 h.

The emulsion obtained in this way is now investigated with regard to particle size, oil viscosity and the content of octamethylcyclotetrasiloxane $D_4$. The results can be found in table 1.

Comparative Example C3

100 parts of an α,ω-hydroxy-terminated polydimethyl-siloxane with a viscosity of 60 mPas are introduced as initial charge in a beaker.

Using a rotor-stator homogenizer (Ultra-Turrax, peripheral speed 16 m/s), 3 parts of alkylbenzene-sulfonic acid (available under the name "Marlonsaure AS 3" from SASOL AG, D-Marl), 3 parts of ammonium lauryl sulfate (available under the name "Disponil ALS 40" from Cognis GmbH, D-Dusseldorf) and 7 parts of water are added and homogenized for 10 min. The resulting gel-like phase is diluted with 100 parts of water over the course of 15 min and stored at 20° C. After 6 h, the emulsion is adjusted to a pH of 7 with triethanolamine.

The emulsions obtained in this way were now investigated with regard to particle size, oil viscosity and the content of octamethylcyclotetra-siloxane $D_4$. The results can be found in table 1.

Comparative Example C4

The procedure described in example C3 is repeated, except that the emulsion was only neutralized after 168 h.

The emulsions obtained in this way were now investigated with regard to particle size, oil viscosity and the content of octamethylcyclotetra-siloxane $D_4$. The results can be found in table 1.

Comparative Example C5

The procedure is in accordance with the teaching of DE-A 2730923. 100 parts of a polydimethylsiloxane with a viscosity of 5000 mm²/s are introduced as initial charge and 15 parts of an octyl decylphosphate with an acid number of 295 mg KOH/g (available under the name "Crodafos 810 A" from Croda GmbH, D-Nettetal) were mixed and heated to 80° C. The clear mixture was cooled to 40° C. and 4 parts of monoethanolamine were added. 120 parts of water were then stirred in; this produced a cloudy solution which had separated into an oil phase and a water phase after 24 h. The oil phase had a viscosity of less than 100 mm²/s and a content of 3.0 mol % $D_4$, 0.4 mol % $D_5$, 0.3 mol % $D_6$ and 2.4 mol % $Me_3Si$—O— and $Me_2(OH)Si$—O— end groups, i.e. a chain length of ca. 80. This shows that, in accordance with this method, no stable emulsions are obtainable, but the polydiorganosiloxane is depolymerized, i.e. that in this way in no case can emulsions with highly viscous polydiorganosiloxanes be produced.

The emulsion obtained in this way is now investigated with regard to particle size, oil viscosity and the content of octamethylcyclotetrasiloxane $D_4$. The results can be found in table 1.

TABLE 1

| Example | Particle size D[4,3] in nm | Oil viscosity in mm²/s | $D_4$ in % by wt.* |
|---|---|---|---|
| 1 | 143 | 724,000 | 0.2 |
| 2 | 153 | 1,110,000 | 0.3 |
| 3 | 141 | 1,040,000 | 0.2 |
| 4 | 131 | 1,510,000 | 0.1 |
| 5 | 131 | 1,710,000 | 0.2 |
| 6 | 139 | 978,000 | 0.1 |
| 7 | 141 | 1,050,000 | 0.3 |
| 8 | 394 | 2,520,000 | 0.3 |
| 9 | 138 | 1,390,000 | 0.2 |
| 10 | 130 | 1,260,000 | 0.2 |
| 11 | 344 | 512,000 | 0.2 |
| C1 | 202 | 1,880,000 | 1.7 |
| C2 | 202 | 1,970,000 | 5.4 |
| C3 | 608 | 735,000 | 1.1 |
| C4 | 608 | 2,600,000 | 4.2 |
| C5 | — | <100 | 3.0 |

*based on the high molecular weight polyorganosiloxane of the respective emulsion

Example 12

A shampoo is formulated as follows (the components are named in accordance with INCI nomenclature):

0.2 part of Guar Hydroxypropyltrimonium Chloride (available under the name N-Hance® 3000 from Hercules Inc.) is dispersed in 11.92 parts of water. 71.7 parts of Sodium Laureth Sulfate (available under the name Genapol LRO 26.5% from Clariant GmbH) are stirred in slowly and the mixture is heated to 75° C. In this process, 0.3 part of PEG-150 Distearate (available under the name Emulgin EO 33 from Cognis Deutschland GmbH) is added upon reaching 50° C., and when 65° C. is reached, 1.2 parts of Glycol Distearate (available under the name Genapol PMS from Clariant GmbH) are added. The mixture is mixed until 75° C. is achieved. The mixture is then cooled. When 35° C. is reached, 0.6 part of preservative Kathon CG (available from Acima Chemical Industries Ltd. Inc. CH-9471 Buchs) and 4 parts of the emulsion from example 4 are added and stirred for 5 minutes. Finally, 10.06 parts of Cocamidopropyl Betaine (available under the name Genagen CAB 30% from Clariant GmbH) and 0.56 part of sodium chloride are added and stirred in each case for 10 minutes. This shampoo improves both the dry and wet combability and also the feel to the touch in wet and dry hair.

The invention claimed is:

1. A polyorganosiloxane emulsion comprising
(A) at least one polyorganosiloxane having a viscosity greater than 10,000 mm²/s, measured at 25° C.,
(B) at least one emulsifier of the formula $$(RO)_n P(O)(OH)_{(3-n)} \quad (I)$$

in which
R are identical or different and are monovalent hydrocarbon radicals having 4 to 30 carbon atoms,
n is 1 or 2,
and/or salts thereof
and
(C) water,
with the proviso that the emulsion comprises less than 2% by weight of octaorganylcyclotetrasiloxanes, based on the weight of component (A).

2. The emulsion of claim 1, which comprises less than 1% by weight of octaorganylcyclotetrasiloxanes, based on the weight of component (A).

3. The emulsion of claim 1, wherein the polyorganosiloxanes (A) have a viscosity greater than 100,000 mm²/s, measured at 25° C.

4. The emulsion of claim 2, wherein the polyorganosiloxanes (A) have a viscosity greater than 100,000 mm²/s, measured at 25° C.

5. The emulsion of claim 1, wherein a dispersed phase has a particle diameter of 50 to 1000 nm.

6. The emulsion of claim 1, wherein compounds of the formula (I) are mixtures of diesters and monoesters.

7. The polyorganosiloxane emulsion of claim 1, wherein the polyorganosiloxane has a viscosity of greater than 1,000,000 mm²/s at 25° C.

8. The polyorganosiloxane emulsion of claim 1, wherein at least one polyorganosiloxane is a α,ω-bis(hydroxyl) terminated organopolysiloxane.

9. The polyorganosiloxane emulsion of claim 1, wherein the polyorganosiloxane contains silicon-bonded alkoxy groups.

10. The emulsion of claim 1, wherein the polyorganosiloxane (A) has —OH end groups.

11. The emulsion of claim 1, wherein the polyorganosiloxane (A) has a viscosity of greater than or equal to 1,000,000 mm²/s.

12. The polyorganosiloxane emulsion of claim 1, having a content of octaorganylcyclotetrasiloxane of less than 0.5 weight percent based on component (A).

13. The emulsion of claim 12, wherein in the polyorganosiloxanes (II), $R^1$ is H.

14. A method for producing an emulsion of claim 1, comprising
mixing
(a) polyorganosiloxanes comprising units of the formula $$R^2_a(R^1O)_b SiO_{(4-a-b)/2} \quad (II)$$

in which
$R^2$ are identical or different and are monovalent, optionally substituted hydrocarbon radical having 1 to 30 carbon atoms or hydrogen,
$R^1$ are identical or different and are hydrogen or a monovalent, optionally substituted hydrocarbon radical,
a is 0, 1, 2 or 3 and
b is 0, 1, 2 or 3,
with the proviso that the sum a+b is less than or equal to 3 and the organopolysiloxanes contain 5 to 500 units of the formula (II),
with
(b) at least one emulsifier of the formula (I), the OH groups of which are optionally partially neutralized,
(c) water and
(d) optionally further substances
by stirring and/or homogenization, and condensing the organopolysiloxanes (a) at a temperature of from 0 to 50° C. until a target viscosity is reached, and optionally then neutralizing the emulsifier of the formula (I) with base such that the pH of the emulsion is greater than 5, and optionally adding further water (c) and/or further substances (d).

15. The method of claim 14, wherein
in a 1st step
(a) 100 parts by weight of polyorganosiloxane(s) comprising units of the formula $$R^2_a(R^1O)_b SiO_{(4-a-b)/2} \quad (II)$$

in which $R^2$ are identical or different and are monovalent, optionally substituted hydrocarbon radicals having 1 to 30 carbon atoms or hydrogen, $R^1$ are identical or different and are hydrogen or a monovalent, optionally substituted hydrocarbon radical, a is 0, 1, 2 or 3 and b is 0, 1, 2 or 3, with the proviso that the sum a+b is less than or equal to 3 and the organopolysiloxanes contain 5 to 500 units of the formula (II), (b) 1 to 30 parts by weight of an emulsifier of the formula (I), the OH groups of which are optionally partially neutralized, (c) 1 to 50 parts by weight of water and (d) optionally, further substances are mixed by stirring and/or homogenization, in an optional 2nd step further water (c) is added, in a 3rd step the organopolysiloxanes (a) comprising units of the formula (II) are condensed at temperatures of from 0 to 50° C. until a target viscosity is reached, in an optionally carried out 4th step the emulsifier of the formula (I) is neutralized with base such that the pH of the emulsion is greater than 5, and in an optional 5th step an emulsion obtained in the 4th step is mixed with further water (c) and/or further substances (d).

16. The method of claim 14, wherein, in a first step, the peripheral speed of a stirrer and/or rotor-stator homogenizer is greater than 5 m/s.

17. The method of claim 15, wherein, in the first step, the peripheral speed of a stirrer and/or rotor-stator homogenizer used for mixing is greater than 5 m/s.

18. The emulsion of claim 14, wherein in the polyorganosiloxanes (II), $R^1$ is H.

19. The emulsion of claim 14, wherein in the polyorganosiloxanes (II), a has an average value of from 1.990 to 2.005, and an average value of b from 0.001 to 0.004.

20. The emulsion of claim 19, wherein the polyorganosiloxane (II) has dimethylhydroxysiloxy end groups.

21. A bodycare composition comprising an emulsion of claim 1 in an amount of from 0.05 to 10% by weight.

22. The bodycare composition of claim 21, which is a haircare composition further comprising at least one conditioner.

* * * * *